United States Patent
Mückter

(10) Patent No.: US 7,276,070 B2
(45) Date of Patent: Oct. 2, 2007

(54) OSTEOSYNTHESIS PLATE OR COMPARABLE IMPLANT PLUS BALL SOCKET

(76) Inventor: Helmut Mückter, Eupener Str. 291, 52076 Aachen (DE)

(*) Notice: Subject to any disclaimer, the term of this patent is extended or adjusted under 35 U.S.C. 154(b) by 51 days.

(21) Appl. No.: 10/866,880

(22) Filed: Jun. 14, 2004

(65) Prior Publication Data

US 2005/0004574 A1 Jan. 6, 2005

Related U.S. Application Data

(60) Provisional application No. 60/477,647, filed on Jun. 11, 2003.

(30) Foreign Application Priority Data

Jun. 11, 2003 (DE) ............................. 103 26 643

(51) Int. Cl.
*A61B 17/80* (2006.01)
(52) U.S. Cl. ........................................................ 606/71
(58) Field of Classification Search ............ 623/23.47; 606/69–71
See application file for complete search history.

(56) References Cited

U.S. PATENT DOCUMENTS

| | | | |
|---|---|---|---|
| 4,794,918 A | 1/1989 | Wolter | |
| 5,053,036 A | 10/1991 | Perren et al. | |
| 5,520,690 A | 5/1996 | Errico et al. | |
| 5,607,426 A | 3/1997 | Ralph et al. | |
| 5,954,722 A | 9/1999 | Bono | |
| 6,306,139 B1* | 10/2001 | Fuentes | 606/70 |
| 6,368,320 B1* | 4/2002 | Le Couedic et al. | 606/61 |
| 6,468,278 B1 | 10/2002 | Muckter | |
| 2003/0153912 A1* | 8/2003 | Graf | 606/61 |

FOREIGN PATENT DOCUMENTS

| | | |
|---|---|---|
| DE | 43 41 980 | 6/1995 |
| EP | 0 201 024 | 8/1989 |
| FR | 2 790 198 | 2/1999 |

OTHER PUBLICATIONS

"Universeller Titanfixateur interne", by D. Wolter, U. Schüman, K. Seide (1999) pp. 307-319.

* cited by examiner

*Primary Examiner*—David H. Willse
(74) *Attorney, Agent, or Firm*—Collard & Roe, P.C.

(57) ABSTRACT

To be able to secure a bone screw, in particular one that can be aligned polyaxially, especially fixedly and nevertheless easily and detachably in an osteosynthesis plate or a comparable implant, a clamping bore is proposed in addition to a receiving bore, whereby the receiving bore holds a bone screw directly or indirectly, and the clamping bore runs essentially perpendicular to the osteosynthesis plate or parallel to the receiving bore, and with a recess in the area of the bores, preferably between the bores, being arranged in relation to the receiving bore in such a way that widening of the clamping bore results in a constriction of the receiving bore.

19 Claims, 6 Drawing Sheets

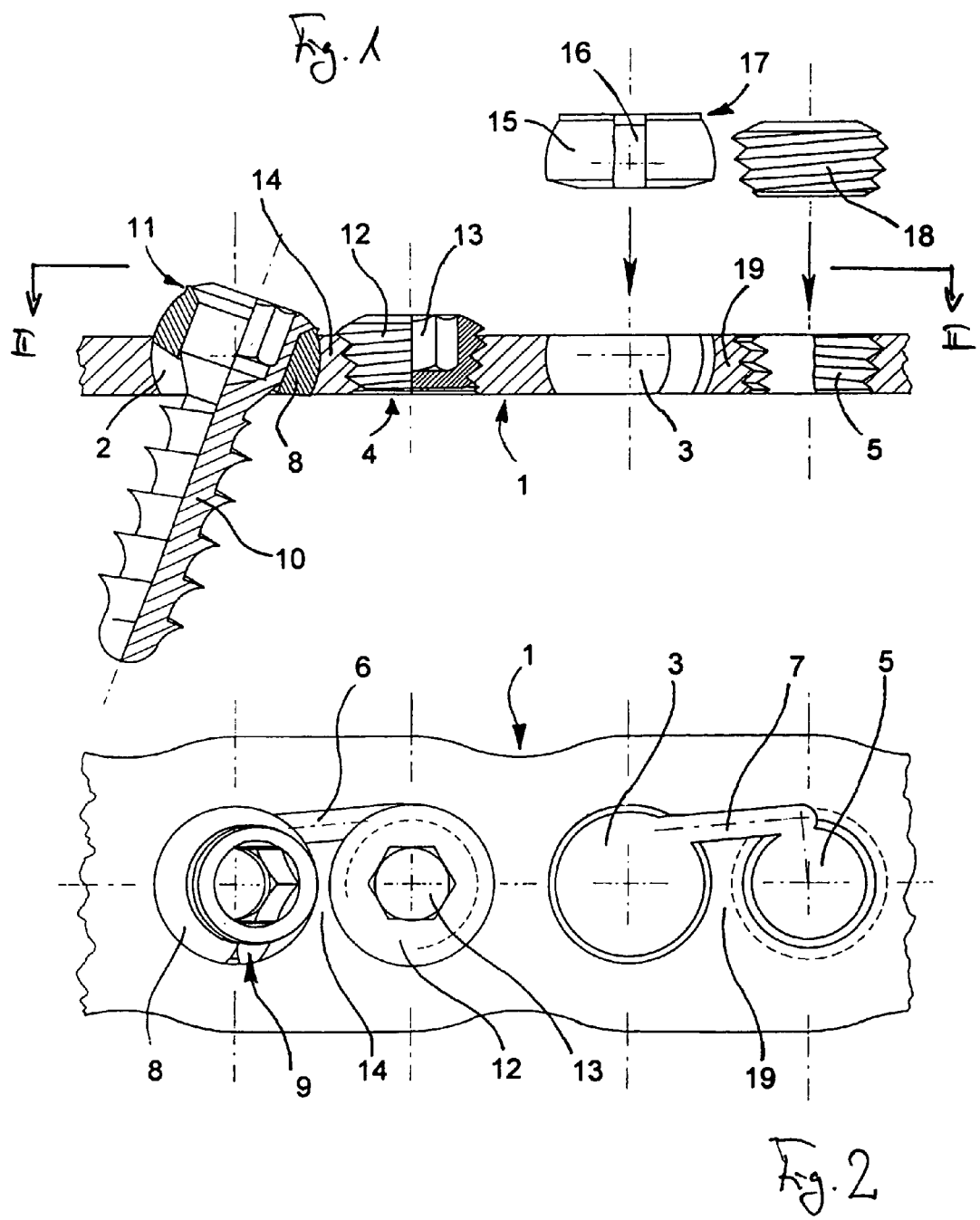

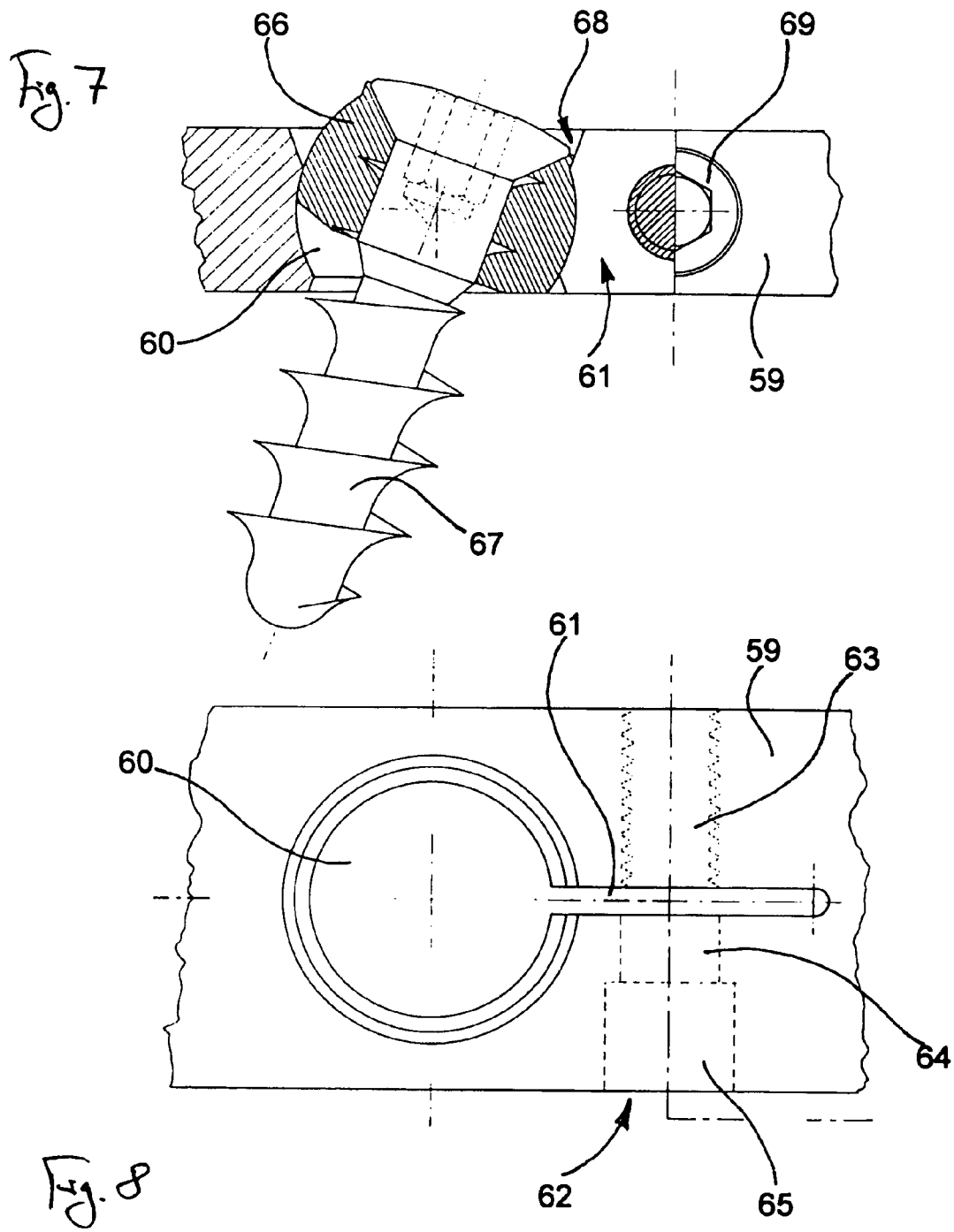

OSTEOSYNTHESIS PLATE OR COMPARABLE IMPLANT PLUS BALL SOCKET

CROSS REFERENCE TO RELATED APPLICATION

Applicant claims priority under 35 U.S.C. §119 of German Application No. 103 26 643.7 filed Jun. 11, 2003. Applicant also claims priority under 35 U.S.C. §119(e) of Provisional Application No. 60/477,647 filed Jun. 11, 2003.

BACKGROUND OF THE INVENTION

1. Field of the Invention

This invention relates to an osteosynthesis plate or a comparable implant plus a ball socket for such an implant.

2. The Prior Art

A problem frequently encountered in orthopedic surgery is that bone fragments which have been separated due to a fracture must be joined together for the purpose of support and/or healing. Osteosynthesis plates and comparable orthopedic implants have proven suitable for this purpose. They have specially designed receiving bores to receive bone screws. The implants are intended in particular for fixation of unstable fractures of large or small tubular bones as well as compact bones such as vertebral bones, wrist bones or ankle bones.

Numerous implants of the generic type in question have been proposed; they can be divided into roughly three groups:

First, traditional osteosynthesis plates with a spherical or conical screw seat or a spherical sliding seat for dynamic compression are known. These are simple plates made of a biocompatible metal into which bone screws can be screwed through predetermined holes in the bones. The holes in the plates are shaped in different forms and have countersunk bores in the form of spherical or conical round bores or spherical sliding holes for centering the screw heads. When the screw is tightened in the bone, the plate is tightened and secured against the bone.

Such plate-screw joints allow almost exclusively the transfer of tensile forces in the direction of the screw axis as well as transverse forces. However, there is no angular stability with this type of plate-screw joint. Therefore, the elementary prerequisite for the use of traditional osteosynthesis plates is an adequate gripping strength of the screw thread in the bone, which makes it possible to secure the plate tightly enough against the bone. In particular in osteoporosis and in the joint area of tubular bones, however, it is often impossible to achieve adequate holding forces of the screw thread in the bone. Then the screws may become loosened and the bone fragments may become tilted, resulting in failure of the implant.

In addition, there are known monoaxially stable plate-screw joints, where bone screws are screwed into the bone through bores in the osteosynthesis plate at a certain angle that is predetermined by the structure. These bores are designed so that the screws are secured in the osteosynthesis plate at this predetermined angle. This makes it possible to hold even compact bone fragments at a fixed angle in relation to the bone plate in the case of periarticular fractures without having to secure the plate against the bone. The periosteum is advantageously protected in this way. Such implants are known from U.S. Pat. 5,053,036, U.S. Pat. 6,468,278 B1 and German Patent DE 43 41 980 A1, for example.

However, one disadvantage of the monoaxially stable plate-screw joint is that the osteosynthesis plate must be aligned very accurately on the bone because of the fixed plate-screw angle. Even minor misalignment of the plate can cause misalignment of the screws that cannot be corrected.

Finally, various embodiments of polyaxially stable plate-screw joints are known from U.S. Pat. No. 5,053,036, French Patent 2,790,198, U.S. Pat. No. 5,954,722, U.S. Pat. No. 5,520,690 and U.S. Pat. No. 5,607,426. The bone screws here are screwed into the bone through bores in the osteosynthesis plate at an angle that can be selected within certain limits of freedom. Since the screws do not naturally have any angular stability at first, they are secured at the previously set angle by means of lockable split taper sockets, which are between the screw and the bore in the plate. The outside surface of the split taper socket and/or the outside surface of the screw head has a spherical shape to ensure free angular mobility.

An alternative approach to free angular mobility without the need for split taper sockets is described by Wolter, Schumann, Seide (1999): The Universal Titanium Fixator; Trauma Berufskrankheiten [Trauma, Occupational Diseases] 1, 307-19. A thread is created in the bore by a tool without creating chips and a bone screw is then screwed through this bore. However, the final direction of the screw is defined without any play when the thread is created.

With the known implants, a fundamental distinction must be made between those that can exert tensile forces on the bone and those that are merely screwed into the bone. With many indications, it is important for the fracture position to secure the bone fragment by tightening the bone screw against the osteosynthesis plate in a targeted manner to thus achieve an anatomically correct position of the respective bone fragments predetermined by the shape of the plate. Of the embodiments cited, this is possible only with the implants according to U.S. Pat. No. 5,520,690 and the very similar U.S. Pat. No. 5,607,426. However, the implants proposed there have a relatively great structural height in the area of the screw head due to the design, so that the use spectrum is limited, in particular in cases of unfavorable soft tissue coverage.

For fixation of bone screws in any directions, European Patent 0 201 024 A1 discloses an arrangement in which a first plate is in contact with the bone and receives a bone screw polyaxially in a receiving bore, whereby the receiving bore is dimensioned in relation to the head of the bone screw so that the head projects above the first plate. After tightening the bone screw, a cover plate is to be placed on this projecting head and tightened by screwing it against the first plate. Due to the pressure of the head of the bone screw through the cover plate, this creates a frictional engagement between the head of the bone screw and the first plate, causing a directionally rigid connection according to the statements in this document. Here again, however, a relatively great structural height is unavoidable due to the design. Furthermore, this design is relatively complicated and is therefore expensive to manufacture.

The object of the present invention is to design an implant—without restricting the freedom in the angle of the bone screws—i.e., without restricting the conventional use of a particular type of implant—so that the bone screws can be secured particularly reliably and nevertheless easily with the smallest possible plate thickness and the smallest possible total structural height in the area of the bone screws. An example of a conventional use of a type of implant should also include in particular the possibility of being able to exert tensile forces on the bone when the bone screw is screwed into the bone so that the osteosynthesis plate can be tightened against the bone and thus a secure fixation between the bone and the osteosynthesis plate can be achieved.

This object is achieved by an osteosynthesis plate or a comparable orthopedic implant with a receiving bore and a clamping bore, whereby the receiving bore is oriented for holding a bone screw directly or indirectly, and the clamping bore runs essentially perpendicular to the osteosynthesis plate or parallel to the receiving bore. A recess is arranged in the area of the aforementioned bores, preferably between the bores, in relation to the receiving bore and to the clamping bore such that widening of the clamping bore causes a constriction of the receiving bore. Directly holding the bone screw is understood to mean that no split taper socket is arranged between the bone screw and the receiving bore, but instead the two are in direct contact. When it is held indirectly, however, the bone screw is inserted into a clamping screw, which in turn sits in the receiving bore.

SUMMARY OF THE INVENTION

The receiving bore is referred to as constricted when a free diameter reduces the size of the receiving bore. In particular, the receiving bore may lose its formerly round shape, so that even a bone screw and/or a split taper socket which originally fills out the receiving bore in its free diameter undergoes a corresponding deformation—essentially radially—whereupon a correspondingly great frictional engagement holds the screw.

A widening of the clamping bore occurs when at least a part of the clamping bore is enlarged radially in comparison with the original state. Imagine, purely as an example, a widening, for example, by screwing a locking screw into a clamping bore, when at least one of the components has a conical design.

A recess may be any change in cross section or material in the plate which weakens the plate with respect to bending, i.e., in which the planar moment of inertia and/or the E-modulus is reduced in comparison with an area otherwise present in the plate or a neighboring area in particular. If the cross section is uniform, a recess may therefore also be an element comprising a weaker material that is flush with the metal of the plate. Of course, a reduction in the cross section of the plate material that has a direct effect on the planar moment of inertia is easier to manufacture. A recess, i.e., a controlled weakening in the body of the plate, directs the area of influence of the deformation at the clamping bore in the direction of the weakening in a targeted manner, so there is a particularly great deformation, i.e., resulting in a particularly great constriction, at the receiving bore. In addition, other areas of the plate undergo as little deformation as possible, and thus the risk of breakage of the plate is prevented to the best possible extent. Targeted deflection of the deformation is observed in particular when the recess is between the bores. However, even a recess in the area of the clamping bore can cause great deformation of the desired type.

The clamping forces achieved at the receiving bore through this invention are greater by several dimensions with a suitable design than the holding forces known in the state of the art. To this extent, the user of the inventive implant can utilize the independent tightening possibility of the bone screw in the receiving bore well to align the plate and/or the bone screws initially with excellent precision adjustment and, if necessary, to tighten the bone against the implant by tightening the bone screws. When the bone screws are finally secured in place, the user must then not apply any direct forces on the bone screws that could cause displacement of the bone screws in their position with respect to the bone or the plate. Instead, this invention makes it possible for the user to easily and indirectly apply even very great clamping forces. Furthermore, the inventive possibility of securing the bone screws is independent of the particular alignment of the bone screws. This is a great advantage, in particular with screws that can be set polyaxially.

The user can reach a clamping element inserted into a clamping bore especially well if it is accessible on the top side of the plate. This is accomplished by the fact that the clamping bore runs essentially perpendicular to the surface of the plate facing away from the bone. If a receiving bore is not arranged essentially at a right angle but instead is at an oblique angle in relation to the surface of the plate, it may be advantageous if the clamping bore with its axis runs at least essentially parallel to the axis of the receiving bore.

To be able to adjust the clamping force more accurately and to be able to loosen tightened screws again with no problem, it is also proposed that with elastic widening of the clamping bore, the constriction of the receiving bore is also elastic. In particular, there should not be any plastic deformation in the area of influence of the widened clamping bore.

Regardless of this, in a preferred embodiment the clamping bore is arranged next to the respective receiving bore such that the distance between the outside diameters of the clamping bore and the receiving bore at its narrowest amounts to at most one clamping bore diameter, preferably at most one-half of a clamping bore diameter, especially preferably at most one-fourth of a clamping bore diameter, preferably at most 2 mm. This ensures that the receiving bore will be in the area of influence of the deformation emanating from the clamping bore, before the deformation has distributed itself too much over the area of the plate with a further distance from the clamping bore and the local deformation assumes only very small dimensions.

In order to achieve the deformations of the receiving bore and the clamping bore that are necessary for effective clamping of a bone screw and a split taper socket which is optionally provided, it is proposed in particular that both the receiving bore and the clamping bore shall communicate directly with a recess in the plate. An especially effective recess is a slot passing through the cross section of the plate.

In a preferred embodiment, a recess is arranged so that it joins the receiving bore and the clamping bore to one another. The recess here may be arranged symmetrically with the connecting axis between the midpoints of the receiving bore and the clamping bore. However, a recess which passes essentially tangentially through both the receiving bore and the clamping bore in the area of its outside diameter is more effective. A narrow web which remains here between the receiving bore and the clamping bore has a base on one side. Such a web can be bent from the clamping bore to the receiving bore with little application of force, thus yielding the constriction of the receiving bore required for securing the bone screw and a split taper socket which may optionally be provided there.

The effect described here is further intensified by an additional recess in the area of the base of the web located between the receiving-bore and the clamping bore. Such an additional recess reduces the planar moment of inertia at the base of the web. The web located between the clamping bore and the receiving bore can thus be bent more easily around the remaining base.

A constriction of the receiving bore can also be accomplished especially effectively by providing a movable clamping body, such as a slide or a movable clamping jaw, between the clamping bore and the receiving bore. It is advantageous here if the movable clamping body is part of the walls of both bores. The main clamping force then flows over the movable clamping body to the receiving bore as soon as the clamping body is at a greater distance from the axis of the clamping bore. The movable clamping body is preferably guided in a recess, whereby this recess may connect the two bores.

The screw-plate joint is at high risk of becoming loosened subsequently when polyaxially securable screws are secured in deviation at too large an angle from the bore axis of the receiving bore. Therefore, a ball split taper socket is advantageously proposed to accommodate a bone screw in a spherical receiving bore of an osteosynthesis plate or a comparable orthopedic implant, said socket having a protruding circular ring collar. Such a circular ring collar limits the maximum angle by which the axis of the ball split taper socket can be pivoted toward the axis of the receiving bore. This provides for the user a visual limit as well as a haptic limit, which can be taken into account quite naturally. The manufacturers of the plate and/or the spherical split taper socket thus have a means of testing certain angles during approval and limiting usage strictly to these angles.

BRIEF DESCRIPTION OF THE DRAWINGS

This invention is explained in greater detail below on the basis of the drawings, in which multiple exemplary embodiments illustrate FIG. 1 a detail in a partially sectional side view of a first osteosynthesis plate with two spherical receiving bores, two neighboring locking bores, a secured bone screw, a separate split taper socket and a separate locking screw, FIG. 2 a detail of the first osteosynthesis plate from FIG. 1 in a top view, FIG. 3 in a top view a detail of a second osteosynthesis plate with a clamping bore and two receiving bores connected directly by recess slots, FIG. 4 in a top view a detail of a third osteosynthesis plate with a clamping bore, which is connected via a recess slot to a receiving bore and at the same time has an additional recess, FIG. 5 in a top view a development of a fourth H-shaped osteosynthesis plate with two different clamping bore-receiving bore arrangements, FIG. 6 in a top view a detail of a fifth osteosynthesis plate with a slot-shaped clamping body in the plate guided between a clamping bore and a receiving bore, FIG. 7 in a partially sectional side view, a detail of a sixth osteosynthesis plate with a secured bone screw in a split taper socket in a receiving bore and a locking screw in a clamping bore running perpendicular to the receiving bore and parallel to the surface of the plate, FIG. 8 a schematic top view of the plate from the detail from FIG. 7, and FIG. 9 a development of a seventh T-shaped osteosynthesis plate with three similar arrangments of clamping bore, receiving bore and recess slot.

The osteosynthesis plate 1 in FIGS. 1 and 2 has two spherical receiving bores 2, 3 and two locking bores 4, 5 in the form of tapered threaded bores with the axes of the bores running parallel to the receiving bores 2, 3. Each of the two spherical receiving bores 2, 3 is connected to one of the locking bores 4, 5 through a slot-shaped recess 6, 7. The slot-shaped recesses 6, 7 are between the respective bores.

DETAILED DESCRIPTION OF REFERRED EMBODIMENTS

Figure 3:
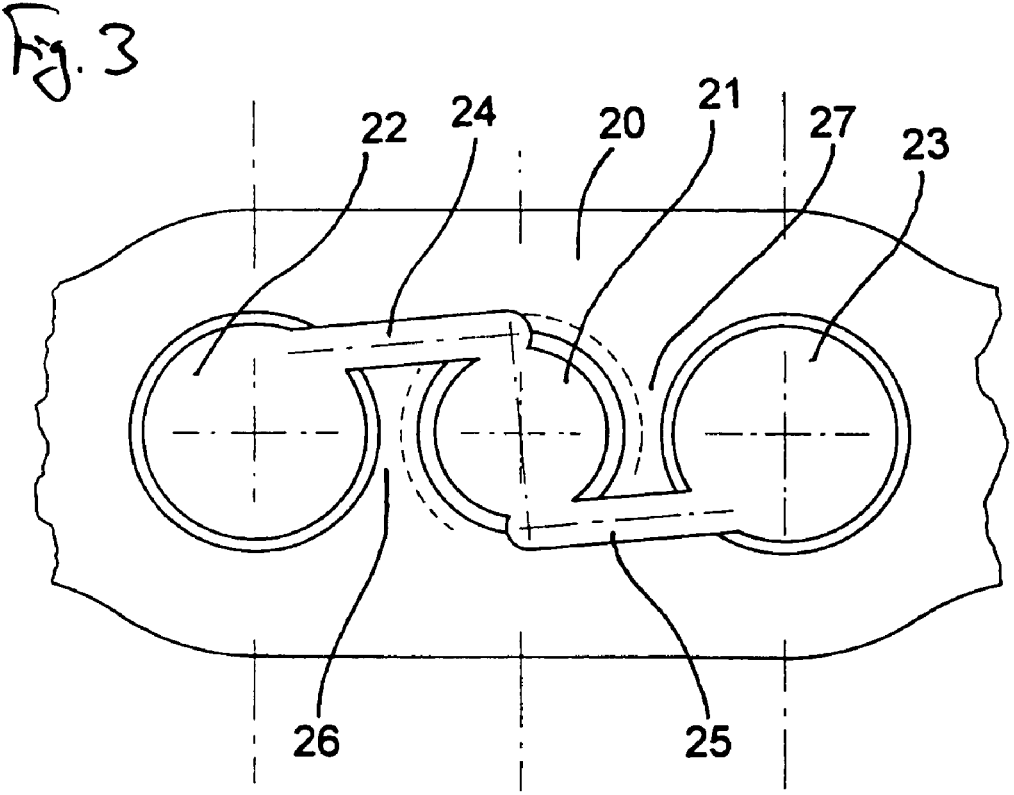

The ball socket 8 fits accurately and rotatably in the spherical receiving bore 2 and is pivotable in all directions. The ball socket 8 has a slot 9, which permits a slight deformation of the ball socket 8. In addition, the ball socket 8 has a central cylindrical bore into which the half-cut bone screw 10 is inserted rotatably and displaceably in clamping seating or play seating.

At its upper end, the ball socket 8 has a circular ring collar 11 which limits the otherwise freely selectable swiveling movement of the screw axis to the desired extent structurally.

A short conical thread pin 12 with a hexagon socket 13 is screwed as a locking screw into the clamping bore 4. By screwing the tapered thread pin 12 into the clamping bore 4, a web 14 is pressed into the spherical receiving bore, so that the osteosynthesis plate 1, the ball socket 8 and the bone screw 10 are tightened against one another. When tapered threaded pin 12 is tightened firmly, this results in an angularly, axially and rotationally stable fastening of the bone screw 10 with respect to the plate 1 in the previously set swivel position of the bone screw 10.

For application of particularly high fastening moments, it is advantageous if the contact surfaces have a rough surface structure between the spherical bore 2 and the ball socket 8, which thereby increases the coefficient of friction.

The spherical receiving bore 3 is empty. It serves to receive the ball socket 15, which is still separate and is of the same design as the ball socket 8. The ball socket 15 is inserted into the receiving bore 3 in the direction of the arrow. To do so, it must be compressed with constriction of a slot 16 to such an extent that its largest diameter can pass by the upper edge of the spherical receiving bore. After insertion of the ball socket 15, it is relaxed again and is correspondingly biased apart, so that it is pivotably guided accurately in the receiving bore 3, limited only by a circular ring collar 17.

The clamping bore 5 is also empty. The tapered threaded pin 18, which is still separate (and is identical to pin 12), is screwed into the clamping bore 5 in the direction of the arrow, so that a web 19 is bent toward the spherical receiving bore 3.

A cam, preferably detachable with self-locking or something comparable may also be used instead of a tapered threaded bore.

The clamping bore 21, embodied centrally as a tapered threaded bore, and the two receiving bores 22, 23 that are symmetrical to it are arranged in the second osteosynthesis plate 20 in FIG. 3. The two receiving bores 22, 23 are each connected directly to the clamping bore 21 via a slot-shaped recess 24, 25. The slot-shaped recesses 24, 25 are elongated and each is connected directly and tangentially to the clamping bore 21. When a tapered threaded pin is screwed into the clamping bore 21, two webs 26, 27 are each pressed toward the receiving bores 22, 23.

In this way, two bone screws can be secured by a locking screw. However, this presupposes that both receiving bores are filled. To do so, however, a filling element may be provided; without having any other function, this filling element would merely fill a receiving bore.

Figure 4:
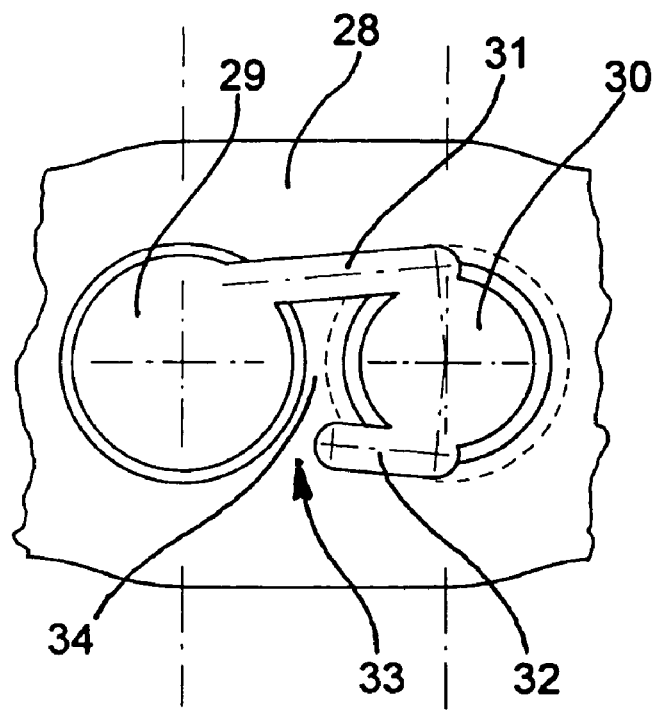

In the third plate 28 in FIG. 4, the receiving bore 29 is connected directly to the clamping bore 30 via the slot-shaped recess 31, essentially tangentially. In addition, the extra recess 32 arranged between the bores is connected only to the clamping bore 30, but it weakens the cross section of the plate at the base 33 of a web 34 of the plate 28 to such an extent that the web 34 can be bent toward the receiving bore 29 due to the small force of the reduced planar moment of inertia.

Figure 5:
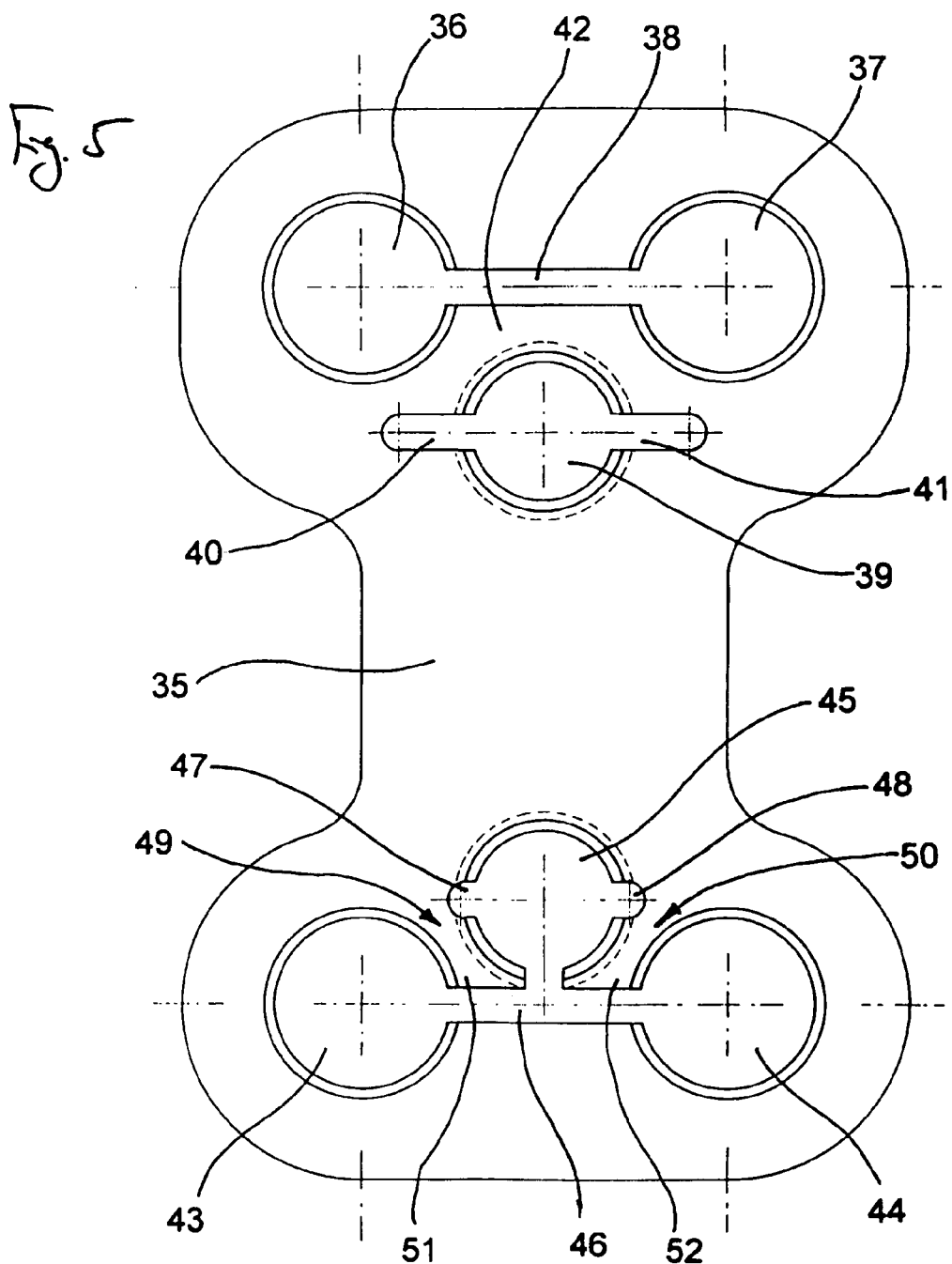

The fourth plate 35 in FIG. 5 preferably provides central stabilization in the area of the cervical vertebrae. Two different variants of screw receptacles with polyaxially stable angles are shown as examples in the upper and lower parts of the H-plate 35. Two spherical receiving bores 36, 37 arranged in the upper section are interconnected by a straight slot-shaped recess 38. A clamping bore 39 is arranged symmetrically with the recess. The clamping bore 39 has two slot-shaped recesses 40, 41, which are arranged parallel to the slot-shaped recess 38. As described above, ball sockets are inserted into the receiving bores 36, 37. By securely tightening a short tapered locking screw into the clamping bore 39, a web 42 is bent toward the upper edge of the H-plate 35, thereby constricting the slot-shaped recess 38 and the two receiving bores 36, 37. In this way, the ball sockets and bone screws used are secured reliably in the plate 35.

There are two receiving bores 43, 44 in the lower section of the plate 35 as well as a clamping bore 45 symmetrical with them. The two receiving bores 43, 44 and the clamping bore 45 are interconnected by a T-shaped recess 46. The clamping bore also has two short extra recesses 47, 48, which narrow the bases 49, 50 of webs 51, 52 and thus reduce the planar moment of inertia.

Figure 6:
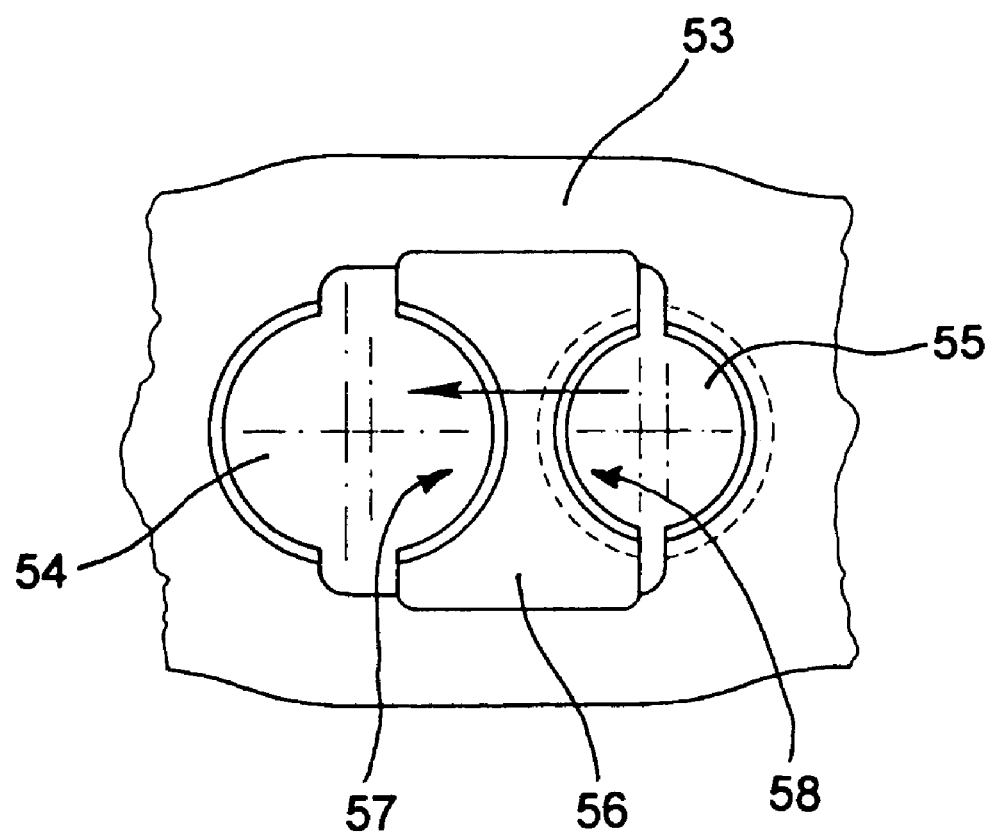

The fifth plate 53 in FIG. 6 again has a spherical receiving bore 54 and a tapered thread bore 55, but each is only designed as approximately a half. Between the receiving bore 54 and the clamping bore 55, each designed as approximately half, a sliding guide is provided for a movable slide-type clamping body 56, which is movably guided forward and backward in the plate 53 in the direction of the arrow.

The slot-shaped clamping body has on one end an approximately half-formed spherical receiving bore 57, which is designed to be congruent with the receiving bore 54, and on the other end it has an approximately half-formed conical clamping thread 58, which is designed to be congruent with the thread flights of the tapered thread 55. By securely tightening a threaded pin or a tapered thread pin, the diameter of the clamping bore 55, 58 is enlarged and the slot-shaped clamping body 56 is shifted in the direction of the arrow toward a ball socket, which is inserted into the receiving bore 54 (not shown), which in turn results in tight clamping of the screw in the plate 53.

The sixth plate 59 in FIGS. 7 and 8 again has a spherical receiving bore 60. A slot-shaped recess 61 is arranged laterally to it. Across the slot-shaped recess 61 there is a screw receptacle 62, which has a thread 63 on one side of the slot-shaped recess 61 and on the other side has a sliding hole 64 and a screw head receptacle 65.

A bone screw 67 is inserted into a ball socket 66 (not shown in FIG. 8), where the resulting unit is freely pivotable up to the limit formed by the circular ring collar 68 on the ball socket 66.

A locking screw 69 (not shown in FIG. 8) inserted into the screw receptacle 62 running in the plate 59 is designed as a hexagon socket screw with a cylindrical head. By tightening the locking screw 69, the slot-shaped recess 61 and consequently also the receiving bore 60 are narrowed, thus ensuring a secure seating of the screw 67, the slotted socket 66 and the plate 59.

Figure 9:
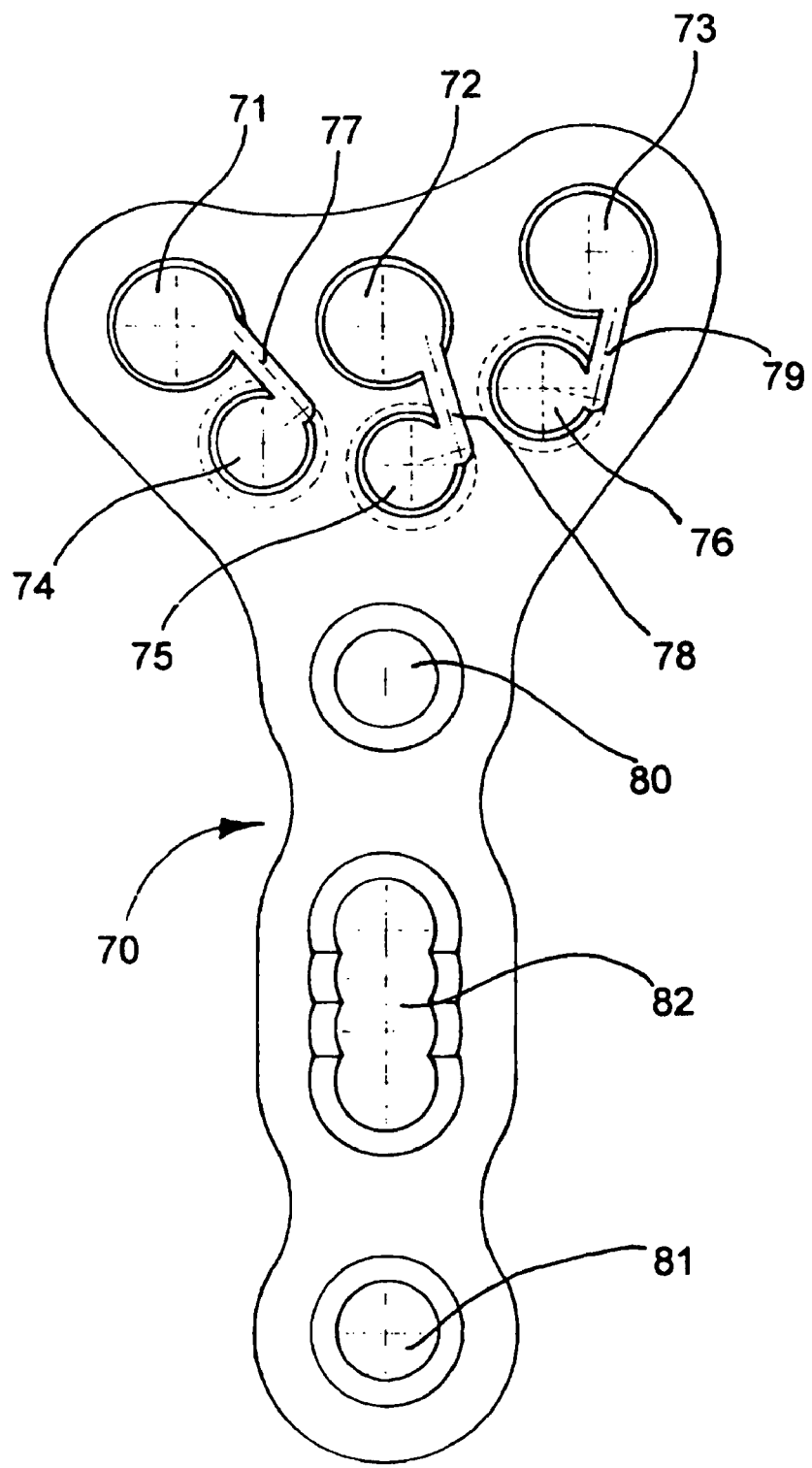

The seventh plate 70 in FIG. 9 is preferably used for stabilizing bone fractures in the area of the distal radius. Three spherical receiving bores 71, 72, 73 and three respective locking bores 74, 75, 76 designed as tapered threaded bores are provided in the widened section of the plate 70 and are joined together by slot-shaped recesses 77, 78, 79. The clamping has already been explained in detail.

Two traditional round holes 80, 81 with spherical countersunk bores to accommodate traditional screw heads and a similarly designed elongated hole 82 are arranged in the thin part of the plate 70.

The invention claimed is:

1. An osteosynthesis plate with a receiving bore and a clamping bore, where the receiving bore is oriented for holding a bone screw directly or indirectly and the clamping bore runs perpendicular to the osteosynthesis plate or parallel to the receiving bore, and with a recess in the area of the bores, which is arranged in relation to the receiving bore and to the clamping bore so that a widening of the clamping bore causes a constriction of the receiving bore.

2. The osteosynthesis plate according to claim 1, wherein the recess is an elongated slot through the osteosynthesis plate.

3. The osteosynthesis plate according to claim 1, wherein the recess is connected directly to the clamping bore.

4. The osteosynthesis plate according to claim 3, wherein the recess is connected tangentially to the clamping bore.

5. The osteosynthesis plate according to claim 1, wherein a recess is connected directly to the receiving bore.

6. The osteosynthesis plate according to claim 5, wherein the recess is connected tangentially to the receiving bore.

7. The osteosynthesis plate according to claim 1, wherein the recess connects the clamping bore and the receiving bore.

8. The osteosynthesis plate according to claim 1, further comprising an additional recess in the area of the bores.

9. The osteosynthesis plate according to claim 8, wherein the additional recess is between the bores.

10. The osteosynthesis plate according to claim 1, characterized by a clamping body between the bores, where the clamping body is part of the walls of both bores.

11. The osteosynthesis plate according to claim 10, wherein the clamping body is guided in a recess.

12. The osteosynthesis plate according to claim 1, wherein for widening the clamping bore it has a cam with a self-locking effect guided in the clamping bore.

13. The osteosynthesis plate according to claim 1, wherein the recess is between the bores.

14. An osteosynthesis plate with a receiving bore and a clamping bore, where the receiving bore is oriented for holding a bone screw directly or indirectly and the clamping bore runs perpendicular to the osteosynthesis plate or parallel to the receiving bore, and with a recess in the area of the bores which is arranged in relation to the receiving bore and to the clamping bore so that a widening of the clamping bore causes a constriction of the receiving bore; wherein the distance between the outside diameters of the clamping bore and the receiving bore at its narrowest point amounts to at most one clamping bore diameter.

15. The osteosynthesis plate according to claim 14, wherein the distance between the outside diameters of the clamping bore and the receiving bore at its narrowest point amounts to at most one-half of a clamping bore diameter.

16. The osteosynthesis plate according to claim 14, wherein the distance between the outside diameters of the clamping bore and the receiving bore at its narrowest point amounts to at most one-fourth of a clamping bore diameter.

17. The osteosynthesis plate according to claim 14, wherein the distance between the outside diameters of the clamping bore and the receiving bore at its narrowest point amounts to at most 2 mm.

18. An osteosynthesis plate comprising a receiving bore, a clamping bore, a plate web having a base, a first recess near said clamping bore and said receiving bore, and a second recess between said receiving bore and said clamping bore at the base of said plate web, said receiving bore being oriented for holding a bone screw directly or indirectly and the clamping bore running perpendicular to the osteosynthesis plate or parallel to the receiving bore, said first recess being arranged in relation to the receiving bore and to the clamping bore so that a widening of the clamping bore causes a constriction of the receiving bore.

19. An osteosynthesis plate comprising a receiving bore, a clamping bore, a tapered thread, a tapered threaded pin screwed into said tapered thread for widening the clamping bore, and a recess near said receiving bore and said clamping bore, said receiving bore being oriented for holding a bone screw directly or indirectly and said clamping bore running perpendicular to the osteosynthesis plate or parallel to the receiving bore, said recess being arranged in relation to the receiving bore and to the clamping bore so that a widening of the clamping bore causes a constriction of the receiving bore.

* * * * *